(12) United States Patent
Gatzemeyer et al.

(10) Patent No.: US 8,813,291 B2
(45) Date of Patent: Aug. 26, 2014

(54) ORAL CARE IMPLEMENT WITH AIR FLOSSING SYSTEM

(71) Applicant: Colgate-Palmolive Company, New York, NY (US)

(72) Inventors: John J. Gatzemeyer, Hillsborough, NJ (US); Eduardo Jimenez, Manalapan, NJ (US); Steve Sorrel, Millwood, NY (US); Philip Durocher, Warren, NJ (US); Bruce Russell, Howell, NJ (US); Thomas Boyd, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/021,891

(22) Filed: Sep. 9, 2013

(65) Prior Publication Data

US 2014/0038127 A1     Feb. 6, 2014

Related U.S. Application Data

(63) Continuation of application No. 12/255,985, filed on Oct. 22, 2008, now Pat. No. 8,539,630.

(60) Provisional application No. 60/981,617, filed on Oct. 22, 2007.

(51) Int. Cl.
| | |
|---|---|
| *A46B 9/04* | (2006.01) |
| *A61C 15/00* | (2006.01) |
| *A46B 13/04* | (2006.01) |
| *A61C 17/022* | (2006.01) |
| *A61C 17/02* | (2006.01) |
| *A61C 17/22* | (2006.01) |
| *A61C 1/00* | (2006.01) |
| *A61C 19/06* | (2006.01) |
| *A61C 17/34* | (2006.01) |

(52) U.S. Cl.
CPC ............... *A61C 15/00* (2013.01); *A61C 17/227* (2013.01); *A61C 17/0217* (2013.01); *A61C 1/0092* (2013.01); *A61C 19/063* (2013.01); *A61C 17/0205* (2013.01); *A61C 17/022* (2013.01); *A61C 17/0202* (2013.01); *A61C 17/3481* (2013.01)
USPC ......... 15/24; 15/22.2; 15/29; 15/405; 433/80; 433/88; 433/89

(58) Field of Classification Search
CPC .... A61C 17/00; A61C 17/227; A61C 17/022; A61C 17/0217; A61C 17/0205; A61C 17/0202; A61C 17/02
USPC ......... 15/22.1, 22.2, 23, 24, 28–29, 344, 405; 433/80, 84, 87–89; 601/154–155, 601/161–163, 165
See application file for complete search history.

(56) References Cited

U.S. PATENT DOCUMENTS

| | | | |
|---|---|---|---|
| 2,813,529 | A | 11/1957 | Janis-Indrikis |
| 3,178,754 | A | 4/1965 | Cleverdon |
| 3,195,537 | A | 7/1965 | Blasi |
| 3,592,244 | A | 7/1971 | Chamberlin |
| 3,823,710 | A | 7/1974 | Borden |
| 4,141,352 | A | 2/1979 | Ebner et al. |
| 4,151,648 | A | 5/1979 | Hirth |
| 4,319,852 | A | 3/1982 | Bell et al. |
| 4,619,009 | A | 10/1986 | Rosenstatter |
| 4,743,199 | A | 5/1988 | Weber et al. |
| 4,903,688 | A | 2/1990 | Bibby et al. |
| 4,941,298 | A | 7/1990 | Fernwood et al. |
| 5,092,750 | A | 3/1992 | Leroy et al. |
| 5,120,219 | A | 6/1992 | DeFarcy |
| 5,344,317 | A | 9/1994 | Paecher et al. |
| 5,403,105 | A | 4/1995 | Jameson |
| 5,462,099 | A | 10/1995 | Demarest et al. |
| 5,934,904 | A | 8/1999 | Elrod et al. |
| 6,079,954 | A | 6/2000 | Kownacki et al. |
| 6,106,288 | A | 8/2000 | Brassil et al. |
| 6,612,770 | B2 | 9/2003 | Aoyama |
| 6,622,333 | B1 | 9/2003 | Rehkemper |
| 6,689,078 | B1 | 2/2004 | Rehkemper et al. |
| 6,802,097 | B2 | 10/2004 | Hafliger et al. |
| 6,883,564 | B2 | 4/2005 | Risch et al. |
| 6,884,069 | B2 | 4/2005 | Goldman |
| 6,918,153 | B2 * | 7/2005 | Gruber .......................... 15/22.1 |

| | | | |
|---|---|---|---|
| 6,964,569 | B2 | 11/2005 | Nordmo et al. |
| 7,021,930 | B2 | 4/2006 | Schemmer et al. |
| 2001/0029639 | A1 | 10/2001 | Seifert |
| 2002/0108193 | A1 | 8/2002 | Gruber |
| 2002/0123020 | A1 | 9/2002 | Aumuller et al. |
| 2004/0209222 | A1 | 10/2004 | Snyder et al. |
| 2005/0004498 | A1 | 1/2005 | Klupt |
| 2005/0102780 | A1* | 5/2005 | Hohlbein .................. 15/110 |
| 2005/0271531 | A1 | 12/2005 | Brown et al. |
| 2006/0021165 | A1 | 2/2006 | Boland et al. |
| 2006/0078844 | A1* | 4/2006 | Goldman et al. ............ 433/80 |
| 2007/0086831 | A1 | 4/2007 | Wold |
| 2007/0113374 | A1 | 5/2007 | Joshi |

FOREIGN PATENT DOCUMENTS

| | | |
|---|---|---|
| DE | 4226419 | 5/1993 |
| DE | 102 21 021 | 11/2003 |
| DE | 10 2006 015691 | 10/2007 |
| WO | WO 94/08533 | 4/1994 |
| WO | WO 2004/058002 | 7/2004 |
| WO | WO 2005/058187 | 6/2005 |
| WO | WO 2005058187 A1 * | 6/2005 |
| WO | WO 2006/067760 | 6/2006 |
| WO | WO 2006067760 A1 * | 6/2006 |
| WO | WO 2007/072430 | 6/2007 |
| WO | WO 2007072430 A2 * | 6/2007 |

International Search Report issued in International Application PCT/US2008/080704 mailed May 18, 2009.

* cited by examiner

*Primary Examiner* — Lee D Wilson
*Assistant Examiner* — Tyrone V Hall, Jr.
(74) *Attorney, Agent, or Firm* — Thibault Fayette

(57) ABSTRACT

An oral care implement is disclosed comprising: an oral care region having cleaning elements; a body coupled to the oral care region; a gas outlet operably coupled to a gas source, the gas outlet disposed in the oral care region; an oral care material source storing an oral care material; an oral care material outlet operably coupled to the oral care material source, the oral care material outlet disposed in the oral care region; and wherein the oral care material outlet is spaced apart from the gas outlet. In another aspect, an oral care implement is disclosed comprising an oral care region having an elastomeric tooth cleaning element and an air outlet positioned adjacent the air outlet so that an air stream existing the air outlet causes a dynamic vibratory flexing action of at least a portion of the elastomeric tooth cleaning element.

19 Claims, 8 Drawing Sheets

ORAL CARE IMPLEMENT WITH AIR FLOSSING SYSTEM

CROSS-REFERENCE TO RELATED APPLICATIONS

The present application is a continuation of U.S. patent application Ser. No. 12/255,985, filed Oct. 22, 2008, which in turn claims benefit of U.S. Provisional Application No. 60/981,617, filed Oct. 22, 2007, the disclosures of which are hereby incorporated by reference herein in their entirety.

BACKGROUND OF THE INVENTION

The present invention pertains to an oral care implement, in particular, to a toothbrush with an air flossing system. Individuals exhibit many forms of poor oral health including tooth decay, periodontal diseases and bad breath (halitosis). Tooth decay and periodontal disease are typically caused by harmful bacteria within the mouth. When the harmful bacteria mixes with proteins present in saliva, a film of plaque is formed on the teeth and soft tissue. If the plaque is not removed, it can attack the teeth and create cavities. Additionally, the plaque will attack the soft tissue within the mouth and cause gum disease, the leading cause of tooth loss in adults. Many individuals, especially young children, do not regularly brush their teeth or perform interdental cleaning of their teeth. Such habits often can be attributed to the individual regarding tooth brushing as a mundane duty with few pleasurable aspects.

BRIEF SUMMARY OF THE INVENTION

The present invention pertains to an oral care implement with an air flossing system.

In one aspect, an oral care implement includes an oral care region having cleaning elements for engaging oral tissue. A body is provided for gripping the implement. An air source is disposed in the body for proving pressurized air to an air outlet. The air outlet is disposed in the oral care region for injecting the pressurized air to clean debris from the oral tissue.

In another aspect, an oral care implement includes an oral care region having at least one cleaning element for engaging oral tissue. An air device is provided which delivers pressurized air. An air outlet is disposed in the oral care region and is operatively connected to air device. Further, the oral care implement includes a motion-producing device capable of moving the cleaning element during release of pressurized air from the air outlet.

In another aspect, a docking station for recharging the oral care implement has an air reservoir or an air pump, or both.

In a further aspect, an oral care implement is disclosed comprising: an oral care region having cleaning elements; a body coupled to the oral care region; a gas outlet operably coupled to a gas source, the gas outlet disposed in the oral care region; an oral care material source storing an oral care material; an oral care material outlet operably coupled to the oral care material source, the oral care material outlet disposed in the oral care region; and wherein the oral care material outlet is spaced apart from the gas outlet.

In yet another aspect, an oral care implement is disclosed that comprises: an oral care region having at least one cleaning element; a body coupled to the oral care region; an air source for storing pressurized air; an air outlet disposed in the oral care region and operably coupled to the air source; an elastomeric tooth cleaning element extending from a surface of the oral care region; and wherein the elastomeric tooth cleaning element is positioned on the oral care region adjacent the air outlet so that the air stream causes a dynamic vibratory flexing action of at least a portion of the elastomeric tooth cleaning element.

Other features and advantages of the invention will become apparent from the following description taken in conjunction with the following drawings.

DETAILED DESCRIPTION OF THE INVENTION

In the following description, the invention is discussed in terms of a toothbrush (e.g. a form of an oral care implement) but could be in the form of other personal care implements. For example, a toothbrush can be used for personal hygiene, such as oral care purposes. Further, it is understood that other embodiments may be utilized and structural and functional modifications may be made without departing from the scope of the present invention.

Figure 1:
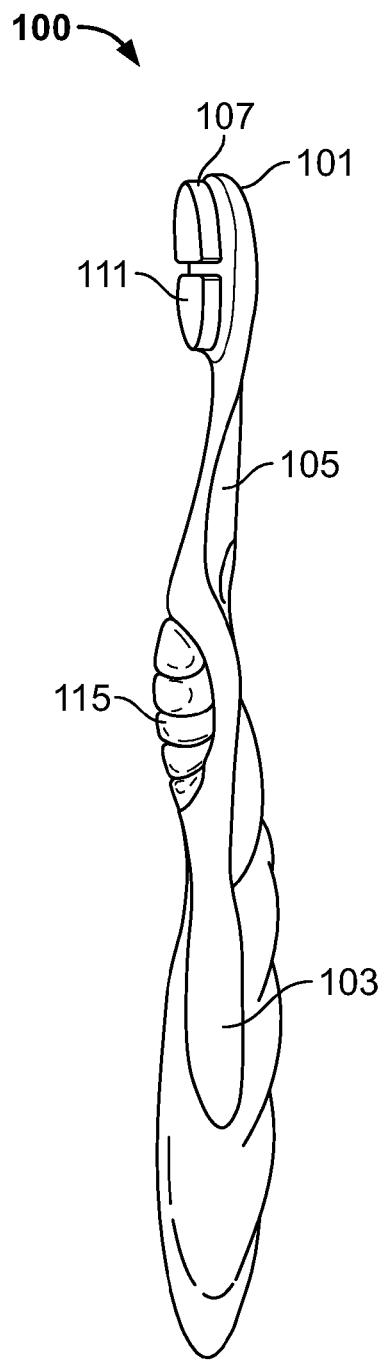
FIGS. 1 and 2 are perspective front and rear views of an oral care implement, such as a toothbrush, according to one or more embodiments of the invention.
Figure 2:
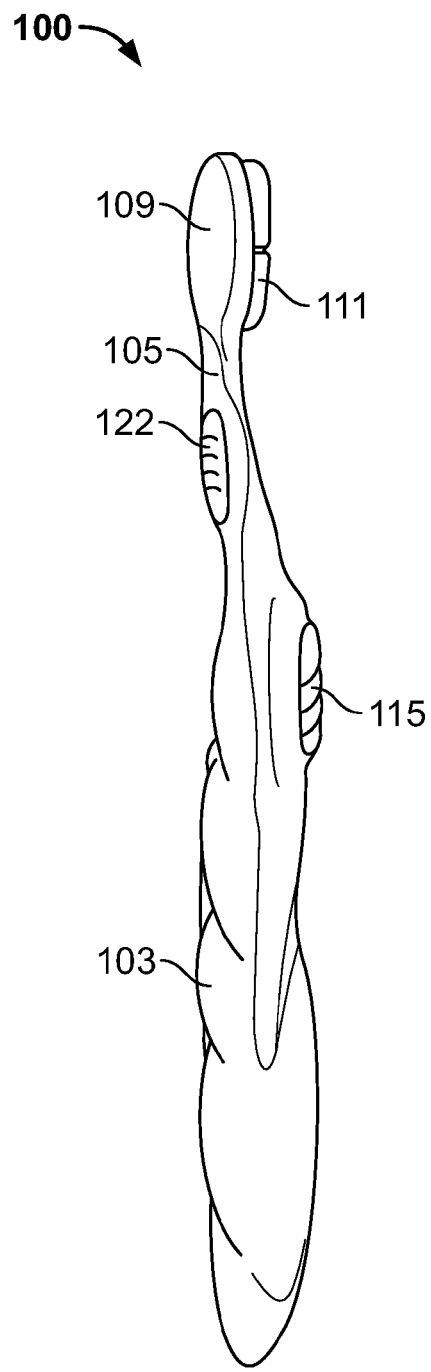

FIGS. 1-2 illustrate an oral care implement, such as a toothbrush, generally designated with the reference numeral 100. The toothbrush 100 generally includes a head 102 and a handle 103.

The handle 103 is generally an elongated member dimensioned so that a user can readily grip and manipulate the toothbrush 100. The handle 103 may be formed of many different shapes, lengths and with a variety of constructions. In one construction, the handle 103 has a neck portion 105 positioned adjacent the head 101. The neck portion 105 may be a narrowed region on the handle 103 between head 101 and the part of the handle normally gripped by the user. Nevertheless, the neck portion 101 could be the region between the head 101 and the part of the handle normally gripped by the user. In another construction, the handle 103 is integrally formed with the head 101. Other attachment configurations also are possible.

The head 101 may include an oral care region comprising one or more tooth cleaning elements 111. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

In one construction, the one or more tooth cleaning elements 111 are formed from a plurality of bristles. Referring to FIGS. 1 and 2, the tooth cleaning elements 111 are bristle regions having different shapes, however, it is understood that a number of different configurations of oral care implements may be utilized. The one or more tooth cleaning elements 111 may be attached to the head 101 by known methods, such as being fit within recesses formed in the head 101 along a front portion 107 of the toothbrush 100 (FIG. 1). The head 101 also may be configured to be detached from the neck 105 or handle 103 and replaced with a new head 101, if desired.

Figure 3:
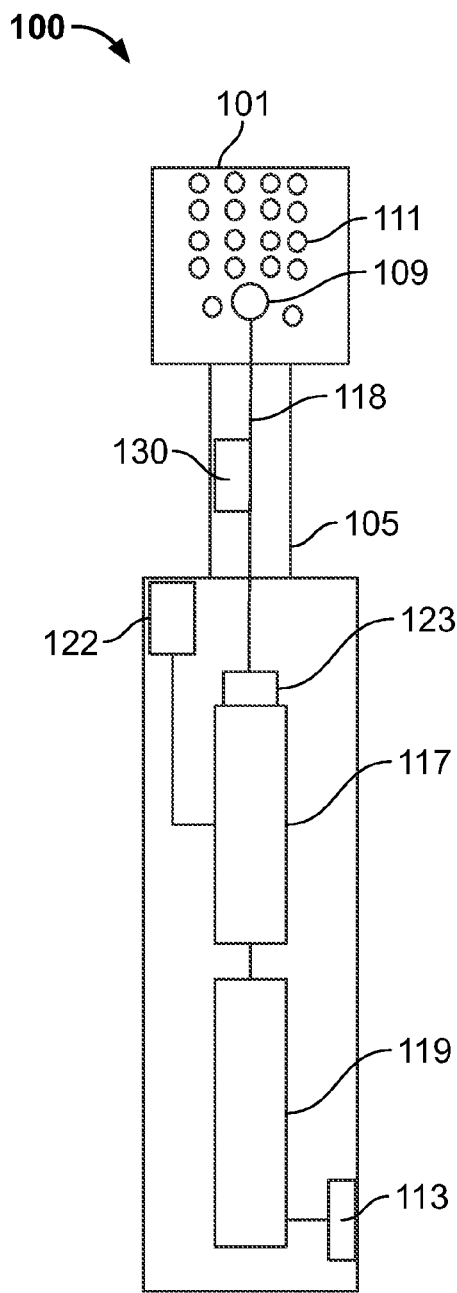
FIGS. 3 and 4 are schematic representations of alternative toothbrush constructions according to one or more embodiments of the invention.

Referring to FIG. 3, toothbrush 100 includes head 101 with an air flossing outlet 109 surrounded by the tooth cleaning elements 111. Toothbrush 100 includes an air inlet 113 for receiving ambient air to be stored in a rechargeable air reservoir or air cartridge 117 for storing pressurized air. In air inlet is connected to an air pump/compressor 119. The both the reservoir 117 and pump/compressor 119 serve as pressurized air sources to air flossing outlet 109. The air inlet 113 may have a filter to trap air borne particulates before storage in the reservoir. To prevent over-pressurizing the reservoir 117, a pressure relief valve 122 may be provided in the handle 103. The relief valve 122 may be preset to open and release air from the reservoir at predetermined pressure, such as 50 to 60 p.s.i. Alternatively, the pump/compressor 419 may be preset to stop operation at a specific pressure or range of pressure in lieu using a pressure relief valve.

Toothbrush 100 may include an air pressure button 115 for controlling pressurized air provided to the reservoir 117. In operation, the engagement of button 115 by the user initiates the operation of air pump/compressor 119. Button 115 may be used for releasing the pressurized air to enable an air flossing operation of the teeth of user. In operation, the button 115 may control the opening and closing of an air valve 123. For example, the air valve 123 may be connected to a relay or solenoid component for opening closing. Also, the air components can be connected together via air conduit 118, such as tubing or other hollow pathway to enable air flow. In an alternative construction shown in FIG. 4, toothbrush 100' may not include a reservoir 117 for pressurized air storage. In such a construction, the pressurized air is directly transferred from the pump/compressor 119 to air outlet 109. Nevertheless in both constructions, the provided pressure at air outlet 109 may range from 15.0 pounds per square inches (p.s.i.) to 30.0 p.s.i.

Figure 5:
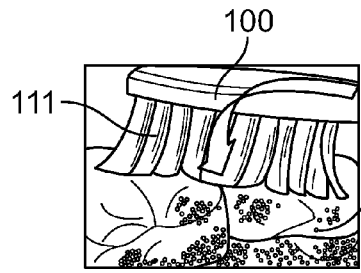
FIGS. 5-7 are a schematic representations of the toothbrush cleaning action in an oral cavity.
Figure 6:
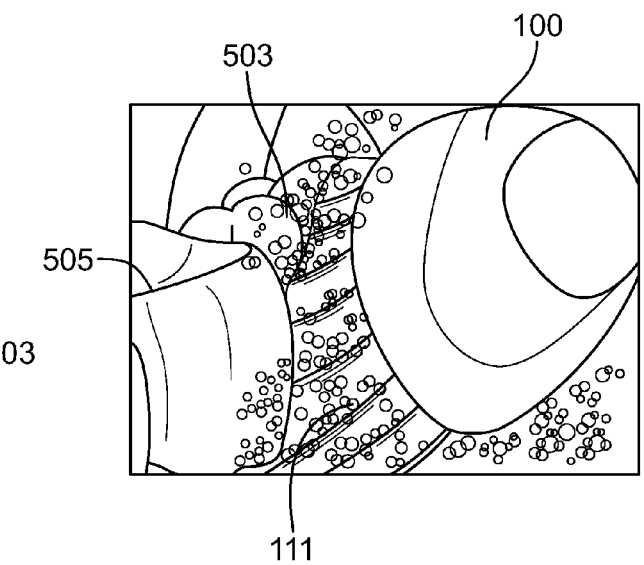
Figure 7:
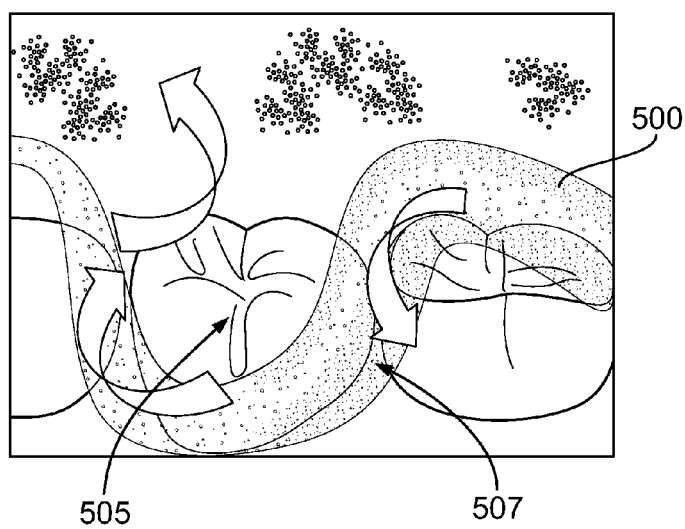

The controlled release of the pressurized air from the outlet 109 provides for interdental cleaning of the teeth of a user. The outlet 109 is provided in the form of an orifice. The orifice can be of different sizes and shapes, such as circular, rectangular, square or triangular. In one construction, the orifice has a circular shape. The diameters of the orifice may range from 0.50 mm to 2.00 mm. Nevertheless, other diameters are possible. Referring to FIGS. 5-7, as can be appreciated in operation, the pressurized air exits from the air outlet 109 in the form of an air stream 500. The air stream can be delivered at a constant rate or could be pulsated at a predetermined rate, as discussed with regard to FIG. 12. The air stream 500 interacts with dentifrice and water within the field of cleaning elements 111. It is understood that the air-dentifrice-water interaction creates a high pressure bubble matrix 503. A schematic representation of flow of air stream 500 and cleaning action is shown in FIG. 7. Referring to FIG. 7, as can be appreciated, the velocity of the bubbles 503 against the tooth surfaces 505 generally conform to the curvature of the teeth, penetrates into the interproximal areas between the teeth and sweeps away the plaque and debris. The loosened plaque and debris are received by the cleaning elements 111 of the head 101. The effective cleaning of the interproximal areas 507 between the teeth provides a floss-like clean. While one air outlet may be used in the toothbrush 100, the inventive aspect may be practiced with a plurality of air outlets, such as two or three outlets.

Figure 8:
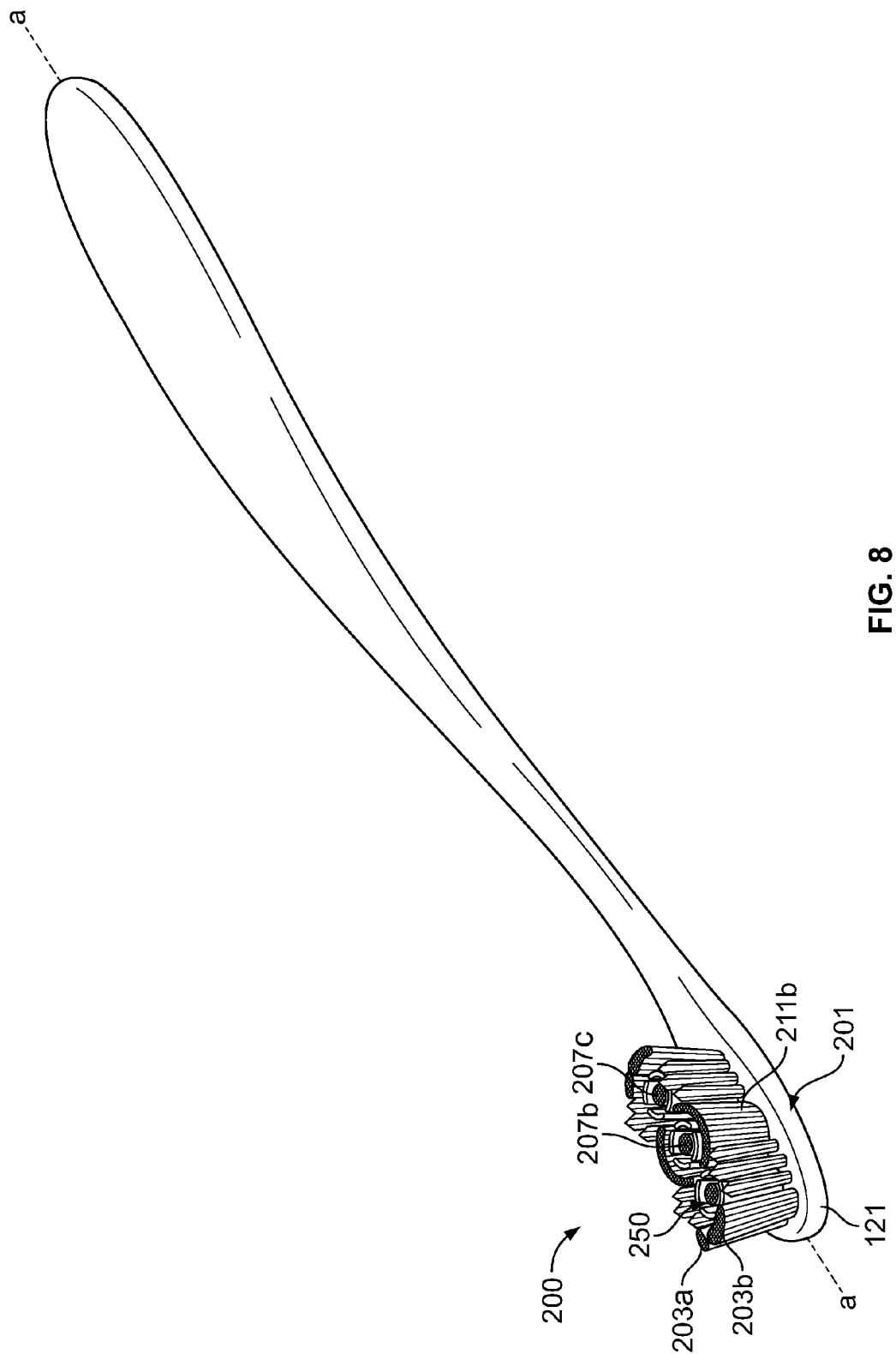
FIGS. 8 and 9 are schematic representations of an alternative toothbrush construction according to one or more embodiments of the invention.
Figure 9:
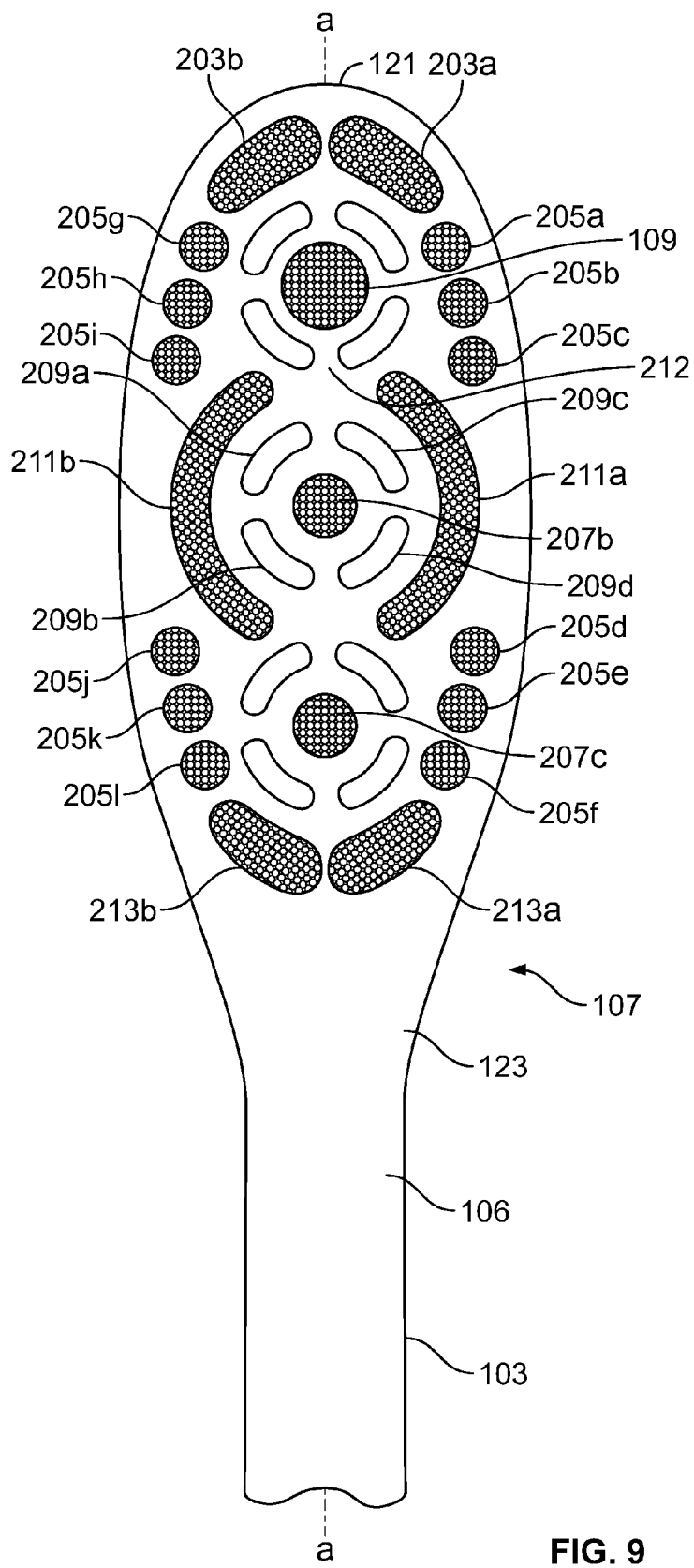

In an alternative construction of the toothbrush 200 shown in FIGS. 8-9, the tooth cleaning elements of head 201 may include a variety of tooth cleaning elements which can be used for wiping, cleaning and massaging the user's teeth and gums. In the illustrated construction of FIG. 12, tooth cleaning elements include distal tooth cleaning elements 203a-b disposed at a distal end 121 of head 201, peripheral tooth cleaning elements 205a-1, longitudinal tooth cleaning elements 207b-c disposed along longitudinal axis a-a, arcuate tooth cleaning elements 209a-d and 211a-b, and proximal cleaning elements 213a,b. Tooth cleaning elements 205, 207, 211 and 213 can be provided as tufts of bristles whereas tooth cleaning elements 209 can be formed as elastomeric walls segments. Nevertheless, other forms and types of tooth cleaning elements may be used.

In this construction, air outlet 109 is provided generally in the center of the arcuate tooth cleaning elements structure near the distal end 121. Nevertheless, the air outlet 109 can be disposed at other locations on the head 201, such as generally in the center of the other arcuate tooth cleaning element structure. In the example of the arcuate elastomeric wall segments, as can be appreciated that the air stream causes a dynamic vibratory flexing action of individual segments with respect to their vertical axis, which in-turn enhances the cleaning action of the distal tip (e.g., wiping edge) of the segment 209 against the tooth surface. Additionally, the interior space defined between the arcuate elements 209 enables the elements to from a nozzle structure/configuration 250 to direct the air stream into the interproximal areas of between the teeth. The gaps 212 formed between the arcuate segments 209a-d enables some controlled flow of the fluid and air flow to other regions of the head 101 during brushing.

It should be appreciated that the nozzle configuration could be formed by tightly packed, elongate bristle tufts. Further, in lieu of gaps between the elements, the nozzle configurations could have completely closed sidewall structures in other constructions. While four arcuate segment cleaning elements 209a-d are shown surrounding each of the generally cleaning elements 207, the inventive aspects may be practiced with more or fewer arcuate segments. While the arcuate segments form a generally circular structure, the segments can form an elliptical shape or a rectangular shape or other shapes in cross-section. Nevertheless, other shapes are possible to form the nozzle-like structure. Hence, the pressurized air stream of toothbrush 100 has synergistic benefits of providing a floss-like clean and improved surface cleaning of the tooth.

The elastomeric material of the cleaning elements has a hardness property in the range of A15 to A35 Shore hardness; A20 to A30 Shore hardness; or A25 to A28 Shore hardness. As an example, one elastomeric material is styrene-ethylene/butylene-styrene block copolymer (SEBS) manufactured by GLS Corporation. Nevertheless, SEBS material from other manufacturers or other materials within and outside the noted hardness range could be used.

Figure 10:
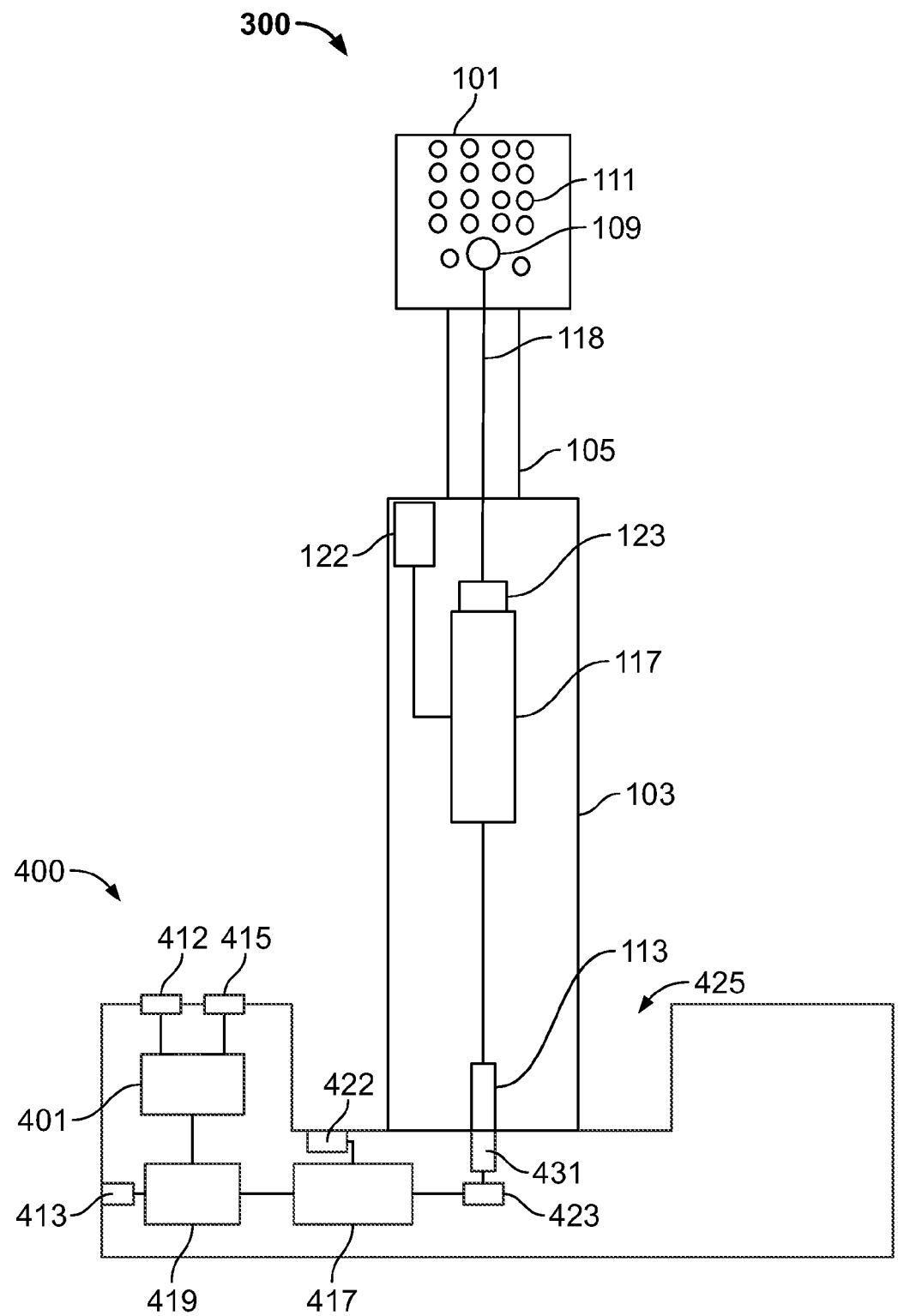
FIG. 10 is a schematic representation of an alternative toothbrush construction according to one or more embodiments of the invention.

Referring to FIG. 10, in an alternative construction, toothbrush 300 may operation in conjunction with a docking station 400. Toothbrush 300 includes the features of toothbrush construction 100, expect for on-board pump/compressor 119. The docking station 400 comprises cavity 452 for seating, receiving and/or storing the handle 103 of the toothbrush 300. The docking station 400 may include an air inlet 413 for receiving ambient air to be stored in a reservoir 417 for storing pressurized air received via the air inlet 413 from air pump/compressor 419. The air inlet 413 may have a filter to trap air borne particulates. To prevent over-pressurizing the reservoir 417, a pressure relief valve 422 may be provided. The relief valve 422 may be preset to open and release air from the reservoir 417 at predetermined pressure, such as 50 to 60 p.s.i. Alternatively, the pump/compressor 419 may be preset to stop operation at a specific pressure in lieu using a pressure relief valve.

Docking station 400 may include an air pressure button 415 for controlling pressurized air entry into the reservoir 417. In operation, the depression or otherwise engagement of button 415 initiates the operation of air pump/compressor 419. Docking station 400 may further include a button 412 for releasing the pressurized air into the rechargeable reservoir in the toothbrush handle 103. In operation, the button 412 controls the opening and closing of an air valve 423 to fill the reservoir 119 of toothbrush 300. An input 431 is operative connected to the air valve 423. Air input 431 works in cooperating with the air inlet 113 of toothbrush 300. The connection between air input 431 and air inlet 113 can be air tight seal based on a threaded connection, press-fit, and the like. Docketing station 400 may include a control system 401 which may comprise one or more printed circuit boards to controlling the operation pump/compressor 419 in conjunction with button 412, 415. In alternative construction, the docking station 400 may not have a reservoir 417 for pressurized air storage. In such a construction, pressurized air is directly transferred to the reservoir of toothbrush handle 103 by the pump/compressor 419 in the docking station 400. In other constructions of the docking station 400, a power source such as a battery or the like, is provided in the interior cavity to power the air storage and filling features. Alternatively, the docking station 400 may to draw electric power from a household outlet.

Referring to FIGS. 1 and 2, toothbrush 100 includes a front portion 107 and a rear portion 109. A thumb gripping portion 115 is provided so that a user may hold the toothbrush 100 with their thumb resting on gripping portion 115. Thumb gripping portion 115 may be formed of a pliable, cushioning material that is depressible as a user presses their thumb against it. In one or more constructions, as described herein, the thumb gripping portion 115 may serves as an actuator to control operation of the toothbrush features. For example, thumb gripping portion 115 may serve as a button to turn control a device associated with the toothbrush 100 "on" and/or "off". For example, the device may be the on-board pump or an air valve for controlling the pressurized air.

In a powered toothbrush construction, thumb gripping portion 115 serves as a button to change a mode of operation of the toothbrush 100. Button 115 enables a user to change the mode of operation to any of a number of different operations. (e.g., an air flossing only mode, a vibratory only mode, or air flossing/vibratory mode). For example, depression or other engagement of button 115 may change the mode of operation to air floss only mode. In the air floss mode, an air stream is provided from the outlet. A subsequent engagement of button 115 may change the mode of operation moving cleaning element mode (e.g., vibratory head or oscillating head portion). A subsequent engagement of button 115 may change the mode of operation to combination air flossing/moving cleaning element mode. Nevertheless, the specific order of the engagement events of the button 115, does not limit the scope of the inventive concepts. Further, the toothbrush 100 may have two or more buttons or actuators for controlling the modes of operation.

In another construction, toothbrush 100 may be a powered toothbrush including motion-producing device that drives a powered element, such as movable cleaning elements 111 with an activation/deactivation or "on/off" button, such as button 115.

Figure 4:
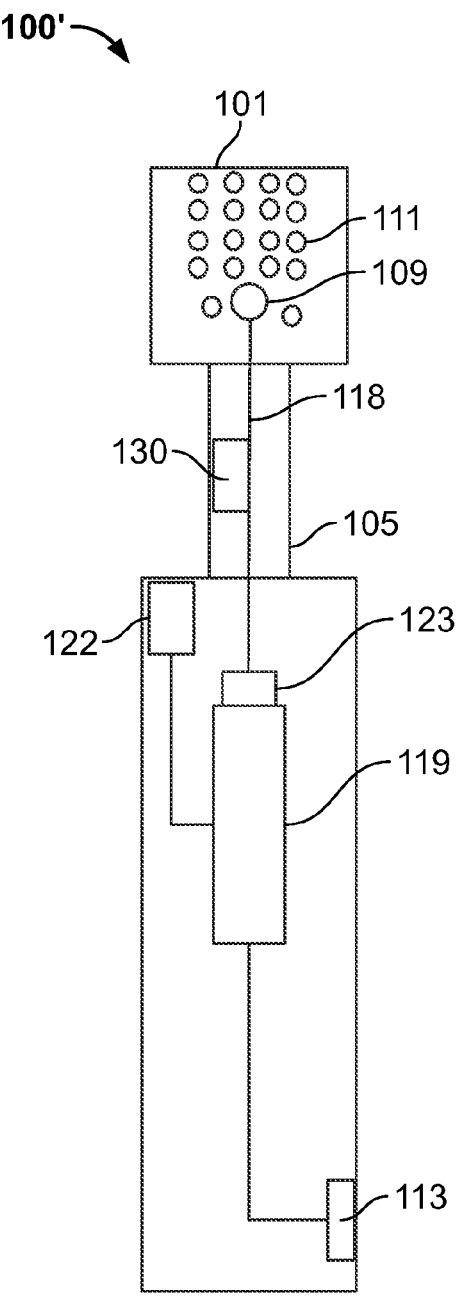

Referring to FIGS. 3-4, in another construction, toothbrush 100 may include a motion-producing device 130 to define a vibratory head 102. A wide variety of motion-producing devices (e.g., vibratory devices) can be used to produce vibrations over a wide range of frequencies. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in head of the toothbrush or neck thereof. When activated, vibratory device is powered by battery (and controlled by electronics on circuit board or switching system) so as to induce vibrations in head of the toothbrush and thereby enhances teeth-cleaning action imparted by the tooth cleaning elements. In alternate constructions, a vibratory device may include a micro motor attached to a shaft, with the shaft coupled to an eccentric rotating about an axis parallel to the longitudinal axis of the toothbrush. In still other constructions, a vibratory-producing device includes an eccentric that is driven by a micro motor in a translatory manner.

A switch, such as a button, toggle switch, rotating dial, or the like, can be provided for activating the vibratory device, such a switch/button 115 of toothbrush 100. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated switch.

Figure 11:
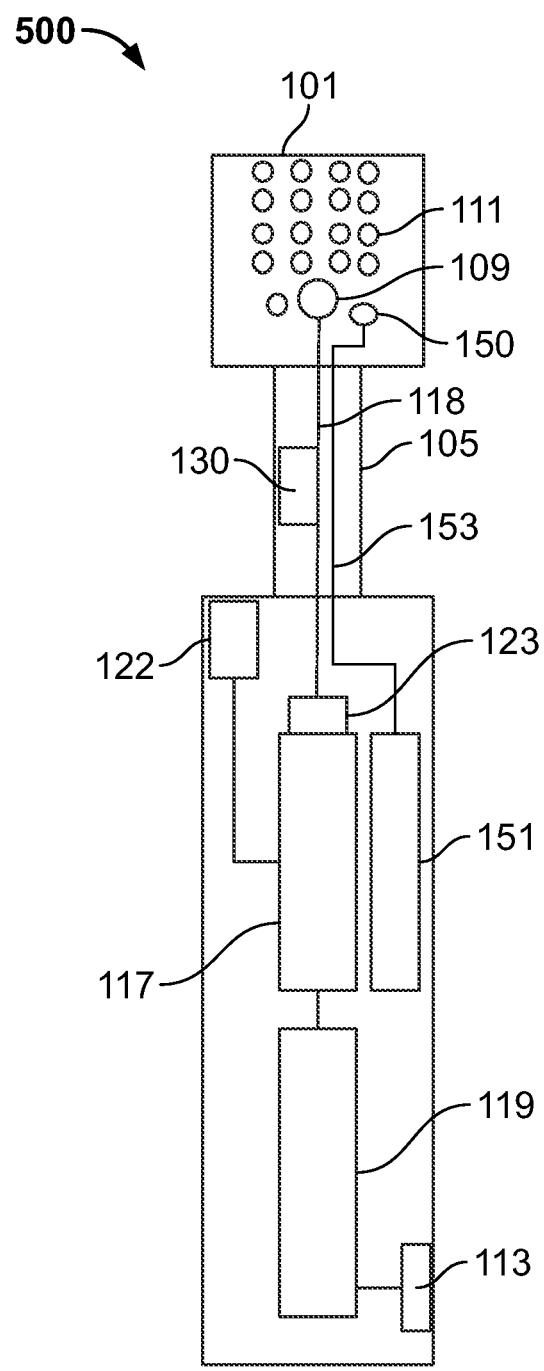
FIG. 11 is a schematic representation of an alternative toothbrush construction and docking station according to one or more embodiments of the invention.

Referring to FIG. 11, in an alternative construction, toothbrush 500 may include an active agent feature. Toothbrush 500 may include the features of toothbrush constructions 100, 100', 200, and 300. An active agent outlet 150 may be provided with the field of cleaning elements 111. The toothbrush 500 can be supplied with one or more cartridges or reservoirs 151 containing active agent(s). Multiple cartridges can be provided, for example, for supplying different active agents or a replacement supply of the same active agent. The outlet 150 is connected to the reservoir 151 via a conduit 153. Depending on the type of active agent used and the location of the air outlet 109 and an active agent outlet, the active agent can be administered before, during, or after initiation of air stream. As can be appreciated, the active agent and air stream interaction on the oral surfaces can improve plaque removal/bacterial removal interdental areas. In one construction, a user-activated switch, such as a dial (not shown), can have multiple settings for selecting one or more of several active agents. For example, the dial can have a first setting for oxidizer/whitener treatment, a second setting for breath freshener treatment, and a third setting for antimicrobial treatment.

Non-limiting examples of active agents which can be used include antibacterial agents, such as chlorhexidine, cetyl pyridininum chloride, triclosan, zinc salts, and; oxidative or whitening agents, such as hydrogen peroxide, urea peroxide, sodium percarbonate, and PVP-$H_2O_2$; supercharged fluoride delivery ingredients; tooth sensitivity ingredients, such as $KNO_3$; occluding agents, such as Novamin® bioactive glass and arginine salts such as arginine bicarbonate; gum health actives, including those which reduce inflammation pathways and/or interfere in bacterial processes which produce inflammatory stimuli, bachalin, polyphenols, triclosan, ethyl pyruvate, and guanidinoethyl disulfide; nutritional type ingredients, such as vitamins, minerals, amino acids, vitamin E, and folic acid; tartar control or anti-stain ingredients, including phosphate salts, polyvinylphosphonic acid, PVM/MA copolymer; enzymes, such as those used for plaque disruption; sensate ingredients, such as those providing cooling, tingle, or heat sensations; flavors and flavor ingredients; anticavity or enamel repair agents; breath freshening ingredients; oral malodor reducing agents; anti-attachment agents, such as ethyl lauroyl arginate; diagnostic solutions, such as plaque-indicator dyes; and combinations thereof.

Examples of flavors and flavor ingredients include essential oils, menthol, carvone, and anethole, and various flavoring aldehydes, esters, and alcohols. Examples of essential oils include oils of spearmint, peppermint, wintergreen, sassafras, clove, sage, eucalyptus, marjoram, cinnamon, lemon, lime, grapefruit, and orange. Flavoring agents typically are provided at a concentration of about 0.1 to about 2 wt % based on the weight of the composition, more usually from about 0.1 to about 0.5 wt %.

The active agent and/or its medium can be selected to complement a toothpaste formula, such as by coordinating flavors, colors, aesthetics, or active ingredients. A flavor can be administered to create a gradual flavor change during brushing, which presently is not possible using toothpaste alone.

The active agent can be provided in any suitable vehicle, such as in aqueous solution or in the form of gel or paste. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B. F. Goodrich, and combinations thereof. The selection of a suitable vehicle will be apparent to persons skilled in the art depending on such factors as the properties of the active agent and the desired properties of the medium, such as viscosity.

Figure 12:
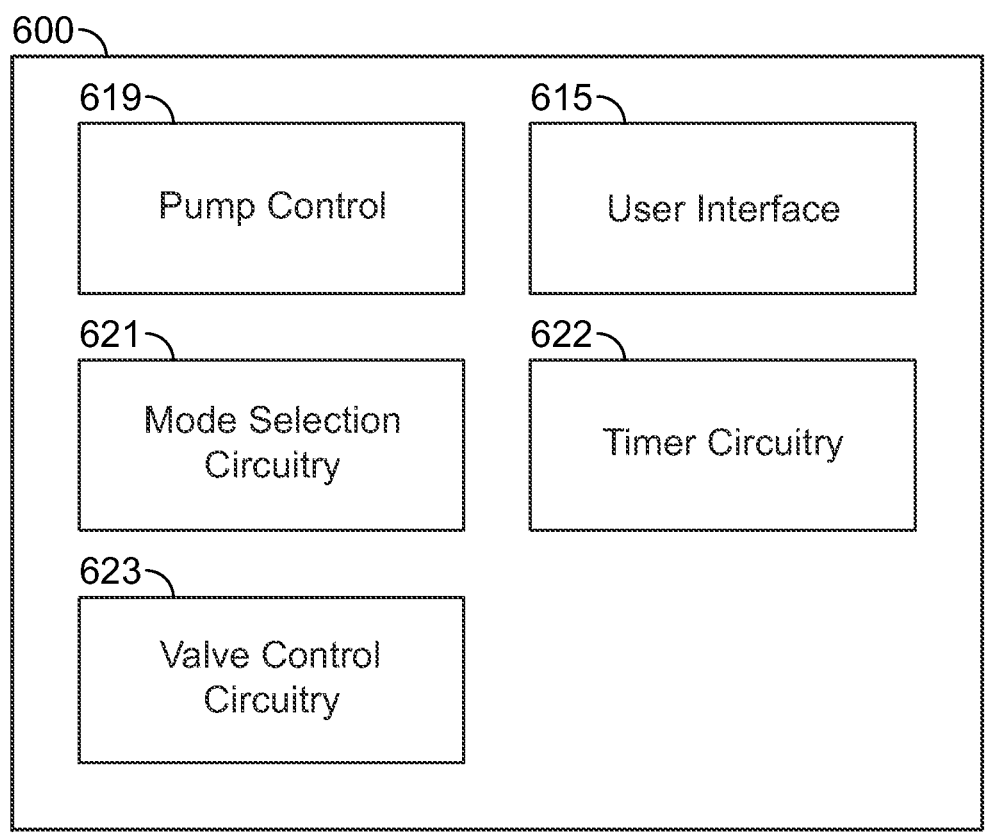
FIG. 12 is an example functional block diagram of components of a control system according to one or more embodiments of the invention.

As described herein with respect to FIG. 12, a control system 600 for toothbrush constructions 100, 100', 200, 300, and 500 may be included to control the air stream for the "floss-like" clean. FIG. 12 illustrates a block diagram of components in one or more constructions of control system 600. One or more of the components shown in FIG. 12 may be included within one or more printed circuit boards. Possible alternatives include flash memory, flash ROM, RAM with battery backup. Control system 600 may include a pump control 619 operatively connected to one or more components of the system 600 and a user interface 615, such button 115.

Mode selection circuitry 621 may include electrical circuitry, software, computer-readable instructions, or other components to allow for changing the mode of operation of the toothbrush 100. For example, mode selection circuitry 621 may receive and process an input signal to change the mode of operation from an air floss mode to moving-cleaning element mode of operation. Mode selection circuitry 621 may be configured to perform the functions for processing signal(s) performing computer-readable instructions, and reading from and writing to a memory (not shown) associated with the toothbrush 100 switching between different modes of operation.

Timer circuitry 622 may include hardware, software, computer-readable instructions, or other components to allow for counting up or counting down time. Timer circuitry 622 may include a crystal oscillator for counting seconds, minutes, etc. Timer circuitry 622 may be configured to perform the functions for processing signal(s) performing computer-readable instructions, and reading from and writing to a memory (not shown) associated with the toothbrush 622 operating in a timer mode for two (2) minutes for air flossing mode. In one arrangement, the air floss mode can end after an elapsed time of 2 minutes.

Control system 600 may include a valve control 623 operatively connected to one or more components of the system 600 to controlling release of air for flossing, including a constant stream of air or pulsating stream of air. The pulsation frequency can may be of different waveforms, including sinusoid, square, sawtooth and like. The control system circuitry 600 may include hardware, software, computer-readable instructions, or other components to enable control the air flow. For example, the control system 600 may include memory of a programmable type in which nonvolatile storage can be electrically erased and reprogrammed.

As discussed, the inventive aspects may be practiced for a manual toothbrush or a powered toothbrush with moving tooth cleaning elements. While the various features of the toothbrush 100 work together to achieve the advantages previously described, it is recognized that individual features and sub-combinations of these features can be used to obtain some of the aforementioned advantages without the necessity to adopt all of these features.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

What is claimed is:

1. An oral care implement comprising;
an oral care region having cleaning elements;
a body coupled to the oral care region;
an air source disposed in the body;
an air outlet operably coupled to the air source for emitting pure air from the air source, the air outlet disposed in the oral care region;
an active agent source disposed in the body and storing an active agent;
an active agent outlet operably coupled to the active agent source, the active agent outlet disposed in the oral care region; and
wherein the active agent outlet is spaced apart from the air outlet.

2. The oral care implement of claim 1, wherein a portion of the cleaning elements defines a nozzle for directing the air, the air outlet disposed within the nozzle.

3. The oral care implement of claim 2, wherein the portion of the cleaning elements comprise elastomeric walls.

4. The oral care implement of claim 2, wherein the portion of the cleaning elements comprise a packed wall of bristles.

5. The oral care implement of claim 1, wherein the air source comprises an air pump operably coupled to the air outlet.

6. The oral care implement of claim 1, wherein the air source comprises a reservoir for storing the air provided to and injected through the air outlet.

7. The oral care implement of claim 6 wherein the body includes a pressure relief valve operably coupled to the reservoir.

8. The oral care implement of claim 1 further comprising a power source operably coupled to a vibratory device, wherein the power source powers the vibratory device for vibrating the cleaning elements.

9. The oral care implement of claim 8, wherein the body includes an actuator, and wherein activation of the actuator changes a mode of operation of the oral care implement between an air floss mode, a vibratory mode, and a combination of air floss/vibratory mode.

10. The oral care implement of claim 1, wherein the air source comprises a reservoir for storing the air, and further comprising a docking station for receiving the body to provide the air to the reservoir.

11. The oral care implement of claim 1, wherein the active agent is selected from the group consisting of antibacterial agents; oxidate or whitening agents; supercharged fluoride delivery ingredients; tooth sensitivity ingredients; gum health actives: nutritional ingredients; tartar control or anti-stain ingredients; enzymes; sensate ingredients; flavors or flavor ingredients; anti-cavity or enamel repair agents; breath freshening ingredients; oral malodor reducing agents; anti-attachment agents; diagnostic solutions; occluding agents; and combinations thereof.

12. An oral care implement comprising:
an oral care region having at least one cleaning element;
a body coupled to the oral care region;
an air source for storing pressurized air disposed in the body;
an air outlet disposed in the oral care region and operably coupled to the air source;
an elastomeric tooth cleaning element comprising a plurality of arcuate wall segments extending from a surface of the oral care region, each of the arcuate wall segments spaced from adjacent arcuate wall segments by a gap, each of the gaps extending from the surface of the oral care region to distal tips of the arcuate wall segments; and
wherein the elastomeric tooth cleaning element is positioned on the oral care region adjacent the air outlet so that an air stream exiting the air outlet causes a dynamic vibratory flexing action of the arcuate wall segments of the elastomeric tooth cleaning element.

13. The oral care implement of claim 12, wherein the elastomeric tooth cleaning element defines a nozzle for directing the air stream, the air outlet disposed within the nozzle.

14. The oral care implement of claim 12, wherein the air source is an air pump operably coupled to the air outlet.

15. The oral care implement of claim 12 further comprising a motion-producing device capable of moving the cleaning element during release of air from the air outlet.

16. The oral care implement of claim 15, wherein the motion-producing device comprises a vibratory device.

17. The oral care implement of claim 15, wherein the motion-producing device comprises an eccentric member with a motor.

18. The oral care implement of claim 12, wherein the body includes an actuator such that activation of the actuator changes a mode of operation of the oral care implement between an air floss mode, a vibratory mode, and a combination of air floss/vibratory mode.

19. An oral care implement comprising:
an oral care region having cleaning elements;
a body coupled to the oral care region;
a gas outlet operably coupled to a gas source for emitting pure gas from the gas source, the gas outlet disposed in the oral care region;
an oral care material source storing an oral care material;
an oral care material outlet operably coupled to the oral care material source, the oral care material outlet disposed in the oral care region; and
wherein the oral care material outlet is spaced apart from the gas outlet.

* * * * *